United States Patent [19]

Kaminka et al.

[11] 4,038,402
[45] July 26, 1977

[54] METHOD OF EFFECTING ANTIHISTAMINIC, ANTISEROTONIN AND ANTIALLERGIC ACTIONS

[76] Inventors: Mikhail Emmanuilovich Kaminka, ulitsa Lobachevskogo, 12, kv. 29; Eva Evseevna Mikhlina, Kutuzovsky prospekt, 5/3, korpus 2, kv. 151; Valentina Yakovlevna Vorobieva, Novo-Alexeevskaya ulitsa, 5a, kv. 13; Anna Dmitrievna Yanina, 2 Karacharovsky proezd, 2, kv. 132; Nadezhda Andreevna Komarova, Shabolovka, 65, korpus, 2, kv. 86; Mikhail Davidovich Mashkovsky, Leningradsky prospekt, 75a, kv. 55; Leonid Nikolaevich Yakhontov, Nakhimovsky prospekt, 1, korpus 1, kv. 22, all of Moscow, U.S.S.R.

[21] Appl. No.: 705,663

[22] Filed: July 15, 1976

Related U.S. Application Data

[62] Division of Ser. No. 542,846, Jan. 21, 1975, abandoned.

[30] Foreign Application Priority Data

Mar. 5, 1974  U.S.S.R. ............................... 2002003

[51] Int. Cl.$^2$ ............................................. A61K 31/445
[52] U.S. Cl. .................................................... 424/267
[58] Field of Search .................. 424/267; 260/501.18, 260/293.53

[56] References Cited

PUBLICATIONS

Tondeur et al., Derives Nouveaux de la quinudidine, Chimica Therapeutica, pp. 207–208 (4) 1966.

*Primary Examiner*—Stanley J. Friedman
*Attorney, Agent, or Firm*—Steinberg and Blake

[57] ABSTRACT

Antihistaminic, antiserotonin and antiallergic effects are achieved by administering to a subject requiring the same a (quinuclidyl-3)-diaryl (heteryl)carbinol of the formula:

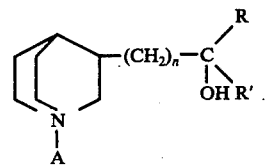

wherein $n$ is 0 or 1, wherein R and R' are the same or different substituted, unsubstituted or hydrated phenyl or heteroaryl and wherein A is either absent or is a physiologically compatible acid such as hydrogen chloride, hydrogen bromide, phosphoric acid, sulphuric acid, maleic acid, adipic acid, citric acid, tartaric acid, benzoic acid, or fumaric acid.

2 Claims, No Drawings

METHOD OF EFFECTING ANTIHISTAMINIC, ANTISEROTONIN AND ANTIALLERGIC ACTIONS

CROSS REFERENCE TO RELATED APPLICATIONS

This is a divisional of our copending application Ser. No. 542,846, filed Jan. 21, 1975, now abandoned, entitled "(Quinuclidyl-3)-Diaryl (Heteryl)-Carbinols, and Their Salts and Method of Preparing Same". A divisional application directed to the production of the compounds is being filed simultaneously with this application.

BACKGROUND OF THE INVENTION (Quinuclidyl-3)-diphenyl carbinol and (quinuclidyl-3)-di-(p-methoxyphenyl)carbinol have been described as having a weak spasmolytic action. This action was indicated as being so weak as to make these compounds relatively useless.

SUMMARY OF THE INVENTION

)-diaryl(heteryl)carbinols accordance with the invention, (quinuclidyl-3)-diaryl(heteryl)carbinols and their salts, having the following formula:

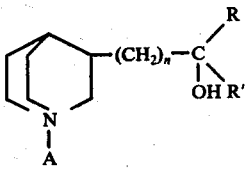

wherein $n$ is 0 or 1, wherein R and R' are the same or different substituted, unsubstituted and hydrated phenyl and heteroaryl, preferably phenyl loweralkoxy phenyl, loweralkyl phenyl, lower dialkyl phenyl, thienyl, cyclohexyl, phenylketone and chlorophenylketone and wherein A is either absent or in a physiologically compatible acid, preferably hydrogen chloride, hydrogen bromide, phospheric acid, sulphuric acid, maleic acid, adipic acid, citric acid, tartaric acid, benzoic acid or fumaric acid is administered to a subject requiring the antihistaminic, antiserotinin, and/or antiallergic action.

It is accordingly a primary object of the present invention to provide for the use of compounds giving antihistaminic, antiserotinin and antiallergic action. It is a further object of the present invention to provide compounds with these actions and with low toxicity.

Other objects and advantages of the present invention will be apparent from a further reading of the specificatiion and of the appended claims.

The compounds which are used to achieve the antihistaminic, antiserotinin and antiallergic effect of the present invention may be produced as described in the parent application Ser. No. 542,846, filed Jan. 21, 1975 or as described in the divisional application Ser. No. 705,664 filed simultaneously with this application. Said applications describe the production, inter alia, of (quinuclidyl-3)-diphenylcarbinol; (quinuclidyl-3)-diphenylcarbinol hydrochloride; (quinuclidyl-3)-diphenylcarbinol hydrobromide; (quinuclidyl-3)-diphenylcarbinol phosphate; (quinuclidyl-3)-diphenylcarbinol sulphate; (quinuclidyl-3)-diphenylcarbinol tartrate; (quinuclidyl-3)-diphenylcarbinol citrate; (quinuclidyl-3)-diphenylcarbinol adipate; (quinuclidyl-3)-diphenylcarbinol maleate; (quinuclidyl-3)-di(2'-methoxyphenyl)carbinol hydrobromide; (quinculidyl-3)-di(2'-methoxyphenyl)carbinol; (quinuclidyl-3)-di(2'methoxyphenyl)carbinol hydrochloride; (quinuclidyl-3)-di(2'-tolyl)carbinol; (quinuclidyl-3)-di(2'tolyl)carbinol hydrochloride; (quinuclidyl-3)-di(3'tolyl)carbinol; (quinuclidyl-3)-di(3-tolyl)carbinol hydrochloride; (quinuclidyl-3-methyl)-diphenyl carbinol; (quinuclidyl-3-methyl)-diphenylcarbinol hydrochloride; (quinuclidyl-3)-di(thienyl-2')carbinol; (quinuclidyl-3)-di(thienyl-2')carbinol hydrochloride; (quinuclidyl-3)-di(4'-methoxyphenyl)carbinol sulphate; (quinuclidyl-3)-di(4'tolyl)carbinol; (quinuclidyl-3)-di(4'tolyl); carbinol hydrochloride; (quinuclidyl-3)-di(3', 4',-dimethyl phenyl)-carbinol; (quinuclidyl-3)-di(3',4'-dimethyl phenyl)-carbinol hydrochloride; (quinuclidyl-3)-di(4'-chlorophenyl)carbinol; (quinuclidyl-3)-di(4'-chlorophenyl) carbinol hydrochloride; (quinuclidyl-3)-(phenyl) (4-tolyl)carbinol; (quinuclidyl-3)-(phenyl)-(4'tolyl)carbinol hydrochloride; (quinuclidyl-3)-(phenyl)-(thienyl)-2')carbinol hydrochloride; (quinuclidyl-3)-(phenyl)(4'-chlorophenyl)carbinol; (quinuclidyl-3) (phenyl) (4'-chlorophenyl)carbinol hydrochloride; (quinuclidyl-3)-(phenyl)-(cyclohexyl)carbinol; (quinuclidyl-3)-(phenyl)-(cyclohexyl)carbinol hydrochloride; (quinuclidyl-3-methyl)-(4'-chlorophenyl)ketone hydrobromide; (quinuclidyl-3)-(2'-chlorophenyl)ketone; (quinuclidyl-3)-(phenyl)-(2'chlorophenyl)carbinol.

DESCRIPTION OF PREFERRED EMBODIMENTS

The pharmacological activity of said compounds has been tested in various experiments in isolated organs and on intact narcotized and non-narcotized animals. The tests were aimed at establishing and quantitatively determining antihistaminic, antiserotonin, cholinolytic, and also broncholytic activity of the preparations. Moreover, the action of the preparations on increased permeability of the vessels, their antiexudative, antiallergic action were tested on guinea pigs, actively sensitized with ovalbumin with the administration of the antigen in the form of aerosol in effective doses. The effect of the preparations on the central nervous system, namely on the spontaneous motor activity, and also the interaction of the preparations with hypnotic and stimulating preparations, was tested.

The toxicity ($LD_{50}$) of the preparations was determined with various methods of administration (intravenous, subcutaneous, in the stomach) on various laboratory animals.

It has been established that various compounds, such as (quinuclidyl-3)-diphenylcarbinol, (quinuclidyl-3-di(-thienyl-2')-carbinol, (phenyl)-(cyclohexyl)-(quinuclidyl-3) -carbinol, (phenyl)-(thienyl-2')-(quinuclidyl-3)carbinol, and others, possess high activity.

Said compounds, in the concentrations of $1\times10^{-8}$ to $1\times10^{-6}$ g/ml prevent spasmogenic action of histamine on the isolated sections of the intestine. When given in a dose of 0.1 – 1 mg/kg to intact narcotized guinea pigs, these compounds prevent, or at least significantly lessen the bronchoconstrictive action of histamine, serotonin, and acetylcholin. In narcotized cats said preparations, given in doses from 0.1 to 0.5 mg/kg, weaken the hypotensive action of histamine. Given to non-narcotized guinea pigs in a dose of 30 mg/kg in the stomach the preparations protect the animals from intoxication with aerosols of histamine (1 percent) and serotonin (1.5 percent). They significantly prolong the latent period of the reaction and decrease the number of lethal outcomes in sensitized guinea pigs with aerosol administration of the effective dose of ovalbumin.

Said compounds produce also anti-edema action to lessen disordered permeability of vessels in rats with subplanter administration of serotonin, formaldehyde, and dextrane. In various conditions of the experiment, these compounds, unlike the known antihistaminic preparations (dimedrol, pipolfen, suprastin) do not affect the activity of the central nervous system — they neither inhibit nor stimulate it.

Some compounds in this series, for example, (quinuclidyl-3)-di(2'-methoxyphenyl)carbinol, (quinuclidyl-3)-diphenylcarbinol, and others, are superior (with respect to certain experimental antihistaminic and antiallergic activity) to the known preparations such as dimedrol and diprasin-pipolfen that are widely used in clinic. Moreover, said compounds are of low toxicity. For example, (quinuclidyl-3)-diphenylcarbinol has high antihistaminic activity and at the same time is 1.5 times less toxic than dimedrol when given in the stomach or intravenously.

(Quinuclidyl-3)-diarylcarbinols having ortho-substitutes in the aryl groups, unlike the other compounds of the same series, have more manifest antiserotonin activity (compared with antihistaminic activity), and they can produce anti-allergic action.

The antiserotonin activity of said compounds was compared with the action of one of the most active known antogonists to serotonin -LSD-25 or diethylamide lysergic acid. It was established that the ortho-substituted derivatives of said compounds are highly active in this respect, and are only 2–10 times inferior to lysergic action diethylamide in other actions.

In experiments on isolated sections of the ileum of guinea pigs, these compounds in the concentrations of $1\times10^{-8}$ - $5\times10^{-8}$ g/ml lessened by 50 percent the spasmogenic action of serotonin. In the concentration of $5\times10^{-8}$ - $1\times10^{-7}$ they decreased by 50 percent the spasmogenic action of histamine and their activity was close to that of dimedrol. Said compounds produce prolonged action: the spasmogenic effect of the antagonists is restored in 40–60 minutes following a single administration.

The broncheal muscle tone was examined in intact narcotized guinea pigs by the Koncett-Rossler method. In these experiments, said compounds were given in a dose of 50–100 mcg/kg intravenously and in 80–95 percent of the cases lessened the bronchoconstrictive action of serotonin. 0.25–0.5 mg/kg doses of these preparations prevented in 80–90 percent of the cases bronchoconstrictive action of histamine and were somewhat more active than dimedrol. Unlike dimedrol and lysergic acid diethylamide, whose effect becomes manifest immediately after their intravenous injection, the above specified doses of said preparations manifest themselves slowly to attain the maximum effect in 1–2 hours which persists for a time; for example the bronchoconstrictive effect of serotonin and histamine does not show till the end of the experiment which indicates that the proposed substances possess prolonged action.

Dimedrol given to guinea pigs in the stomach in a dose of 30 mg/kg 3–4 times increases the latent period of the intoxication reaction caused by aerosols of serotonin and histamine, decreases significantly its intensity and prevents lethal outcomes. The action of the preparations in this dose persists 4–6 hours.

The proposed preparations, in the same conditions of the experiment and in the same dose, prevent in 1–2 hours following administration the development of intoxication and exclude lethal outcomes with serotonin and histamine aerosol poisoning. Their antihistaminic effect persists for 30–35 hours, and the antiserotonin action continues for more than 48 hours.

(Quinuclidyl-3)-di(2'-methoxyphenyl)carbinol given in the stomach in a dose of 30 mg/kg actively protects guinea pigs sensitized with ovalbumin from anaphylactic reaction caused by the aerosol given in the effective dose. The other derivatives were less active in this respect.

Said compounds do not inhibit the central nervous system which makes them superior to dimedrol, pipolfen and other antihistaminic preparations.

While the invention has been described in particular with respect to the pharmacological activity of specific compounds it is apparent that variations and modifications of the invention can be made.

What is claimed is:

1. Method of effecting at least one of the actions of antihistaminic, antiserotonin and antiallergic action, which comprises administering to a subject requiring such action a corresponding effective dose of a compound of the formula:

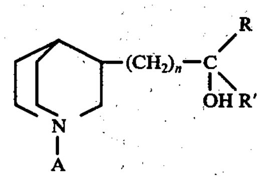

where $n$ is selected from the group consisting of 0 and 1, wherein R and $R_1$ are each selected from the group consisting of phenyl loweralkoxy phenyl, loweralkyl phenyl, lower dialkyl phenyl, thienyl, chlorophenyl, benzoyl, cyclohexyl, phenylketone and clorophenyl ketone, and wherein A is absent or is a physiologically compatible acid.

2. Method according to claim 1 wherein A is present and is a physiologically acid selected from the group consisting of hydrogen chloride, hydrogen bromide, phosphoric acid, sulphuric acid, maleic acid, adipic acid, citric acid, tartaric acid, benzoic acid and fumaric acid.

* * * * *